United States Patent [19]
DeLucia et al.

[11] Patent Number: 5,383,097
[45] Date of Patent: Jan. 17, 1995

[54] CONDUCTIVE PATH ESD SHIELD

[75] Inventors: Paul DeLucia, Baldwinsville; Brian D. Stout, Homer, both of N.Y.

[73] Assignee: Welch Allyn, Inc., Skaneateles Falls, N.Y.

[21] Appl. No.: 141,572

[22] Filed: Oct. 27, 1993

[51] Int. Cl.⁶ .............................................. H05K 9/00
[52] U.S. Cl. ..................... 361/816; 174/35 R; 174/35 MS; 220/402; 361/212; 361/220
[58] Field of Search ............... 174/35 R, 35 MS, 51; 361/818, 816, 212, 220; 257/660; 428/901; 455/90, 100; 128/746; 220/402, 410; 379/437

[56] References Cited

U.S. PATENT DOCUMENTS

| | | |
|---|---|---|
| 2,786,984 | 3/1957 | Slate . |
| 4,667,266 | 5/1987 | Masuoka et al. . |
| 4,688,582 | 8/1987 | Heller et al. . |
| 4,739,453 | 4/1988 | Kurokawa . |
| 4,821,320 | 4/1989 | Andert et al. . |
| 4,831,498 | 5/1989 | Baba . |
| 4,872,091 | 10/1989 | Maniwa et al. . |
| 5,031,076 | 7/1991 | Kiku . |
| 5,170,009 | 12/1992 | Kadokura . |
| 5,171,936 | 12/1992 | Suzuki et al. . |
| 5,206,783 | 4/1993 | Mori et al. . |
| 5,210,395 | 5/1993 | Freeman . |

FOREIGN PATENT DOCUMENTS 4-275493  10/1992  Japan ..................... 361/818

*Primary Examiner*—Leo P. Picard
*Assistant Examiner*—Donald A. Sparks
*Attorney, Agent, or Firm*—Harris Beach & Wilcox

[57] ABSTRACT

An electrostatic discharge (ESD) shield protects sensitive components of a hand-held device where the ESD can enter the unit along a seam or join of the casing halves. The shield employs a insulating film of high electrical strength, e.g., Mylar. This is cut into a sheet that folds for insertion into one casing half. A printed conductive path on the Mylar aligns with the weak zones in the casing, i.e. the seam, and conducts any static charge away from the electronic components, and preferably to a grounding point such as a recharging contact. The region of the insulating sheet adjacent the sensitive circuitry is free of the printed conductive material.

11 Claims, 2 Drawing Sheets

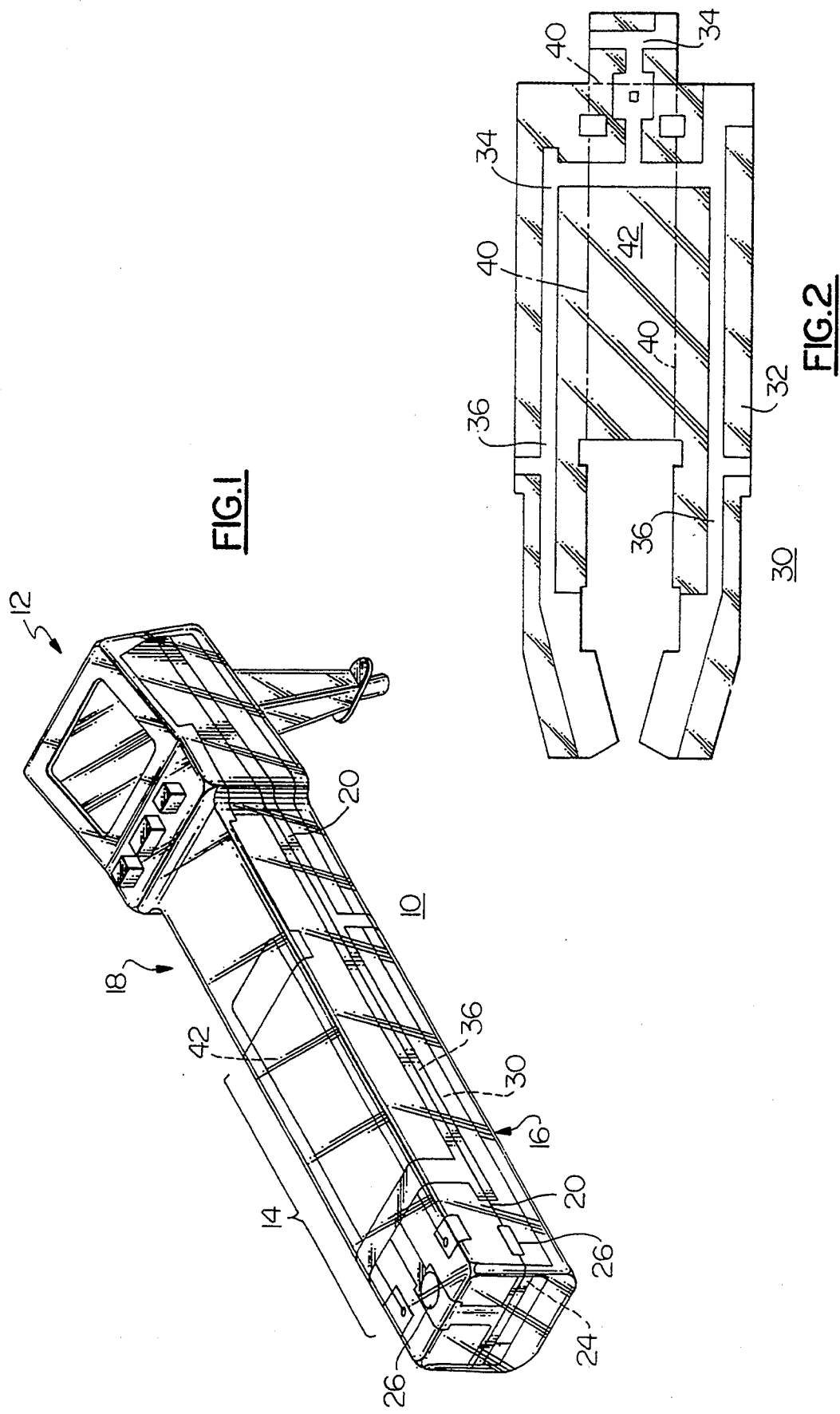

CONDUCTIVE PATH ESD SHIELD

BACKGROUND OF THE INVENTION

This invention relates to the protection of sensitive electronics components from electrostatic discharge (ESD) and is more particularly directed to a barrier that shields internal components of a device from ESD or other high voltage stray charge, and conducts away harmlessly any electrical charge that may find its way into the device.

Modern sophisticated electronic circuits, and particularly integrated solid state circuits based on metal-oxide-semiconductor (MOS) technology, is highly sensitive to electrostatic charge. Great care must be observed in circuit design and construction techniques when MOS circuitry is employed. Even such a simple gesture as touching the MOS integrated circuit package, when protective cautions are not observed, can cause an ESD spark to enter the device and destroy it.

After the circuitry has been installed, the need for ESD protection continues as electrostatic charge build up can occur during use of the electronic instrument. This charge can leak inside the housing of the instrument, so care must be taken to prevent it from reaching and destroying the high-voltage-sensitive electronic components.

In hand-held devices, especially those with plastic cases, ESD is an especial concern. Handling the device, sliding it along a table, or simply picking it up for use can generate electrostatic voltages of 25 kilovolts or more. While the case itself generally has a high electrical strength, there are leakage zones particularly along seams where the lid or cover, that provides access to the electronics, is fitted onto the main housing.

A number of approaches to ESD protection now exist, but these each have significant drawbacks and disadvantages, because they cannot reliably direct the inevitable leakage ESD away from sensitive internal components. These approaches include barriers, laminates, and conductive coatings.

Many high-voltage materials exist that serve as ESD barriers. These include Mylar, Valox, Lexan, Ultem, Nomex, and Kapton, among others. However, a complete barrier is impossible to create for thin materials and films. Therefore these materials require a substantial thickness, i.e. 10 mils or more, for 25 kilovolts of protection. These barriers also permit the electrostatic charge to continue to accumulate, until the voltage exceeds the strength of the barrier.

Laminate barriers employ a film of plastic material and a metal foil layer, and are frequently used in ESD protection or to control electromagnetic interference (EMI). The conductive side is disposed to the outside, i.e. facing the inside of the case, and the insulating side faces inward. These laminate barriers are intended to conduct ESD that enters the case to some grounding means. Unfortunately, because the conductive side extends over the entire shield, the ESD path can come in close proximity to the sensitive electronic components. This can lead to destruction of the very elements that the shield is intended to protect.

Conductive paints and inks are often employed to coat electronic devices for control of EMI, but they may also be employed for ESD protection. These are typically employed by coating the entire case with the conductive paint. As with the laminates, the pathway is not selective, and charge can be carried into proximity to the sensitive components.

Inks are used for EMI control and have been used in circuit board construction, but have not been printed onto a case or onto an insulating barrier.

OBJECTS AND SUMMARY OF THE INVENTION

It is an object of this invention to provide an ESD shield that avoids the drawbacks of the prior art.

It is a more specific object to provide an ESD shield that provides a pathway that conducts static charge away from the sensitive areas of a device.

It is a related object to provide an instrument that contains sensitive electronic components with a shield that guides electrostatic charge along a predetermined pathway while shielding the sensitive components.

It is a further object to produce an effective ESD shield at low cost.

According to an aspect of this invention an ESD shield is provided for protecting an electronic medical diagnostic instrument, such as a tympanometric device, that contains sensitive electronic circuitry that is housed in a plastic casing or housing. The ESD shield could be used to advantage in many devices, but the tympanometric device will serve as an example. The shield comprises a thin sheet or substrate of Mylar or another barrier material of high electrical strength that is dimensioned to fit in the housing. The sheet folds to fit between the electronic circuitry and the lid or cover of the housing. One portion of the sheet covers the region that contains the ESD-sensitive electronic circuitry, and one or more other portions extend along the inside of the joint or seam where the lid or cover meets the base of the housing or case. A printed conductive path is deposited, e.g. by screen printing, on one side of the substrate at the portions that extend along the casing seams. The seams represent regions where charge leakage can occur. The electrostatic charge is guided on the path away from the location of the sensitive components. The printed conductive path can connect to a recharging contact or other means to disperse the electrostatic charge harmlessly. The portion of the sheet or substrate that covers the sensitive components is free of the printed conductive material, so the charge is not conducted near these components.

The sheet should be 10 mils or less, and can be 7 mil Mylar with a strength of about 25 KV, and the conductive path can be a conductive ink such as screen print nickel ink, silver ink, or graphite ink. Because of the action of the conductive path in leading the static charge away, a much thinner shield can be employed in many cases. The shield can have an electrical strength as low as 3 KV and for some applications as low as 1 KV. The shield folds to fit over the electronics circuitry and between the cover and base of the casing. This construction of shield can be installed in devices of new manufacture, or can be retrofitted into existing devices. The shield is also rather economical to manufacture, and does not add significantly to the cost of the device.

The above and many other objects, features, and advantages of this invention will present themselves to those skilled in the art from the ensuing description of one preferred embodiment, which should be read in conjunction with the accompanying Drawing.

BRIEF DESCRIPTION OF THE DRAWING

FIG. 1 is a perspective view of a medical diagnostic instrument having a sensitive electronic circuit contained within a housing, and employing a printed conductive path ESD shield according to one embodiment of this invention.

FIG. 2 is a plan view of the ESD shield of this embodiment.

DETAILED DESCRIPTION OF THE PREFERRED EMBODIMENT

Figure 3:
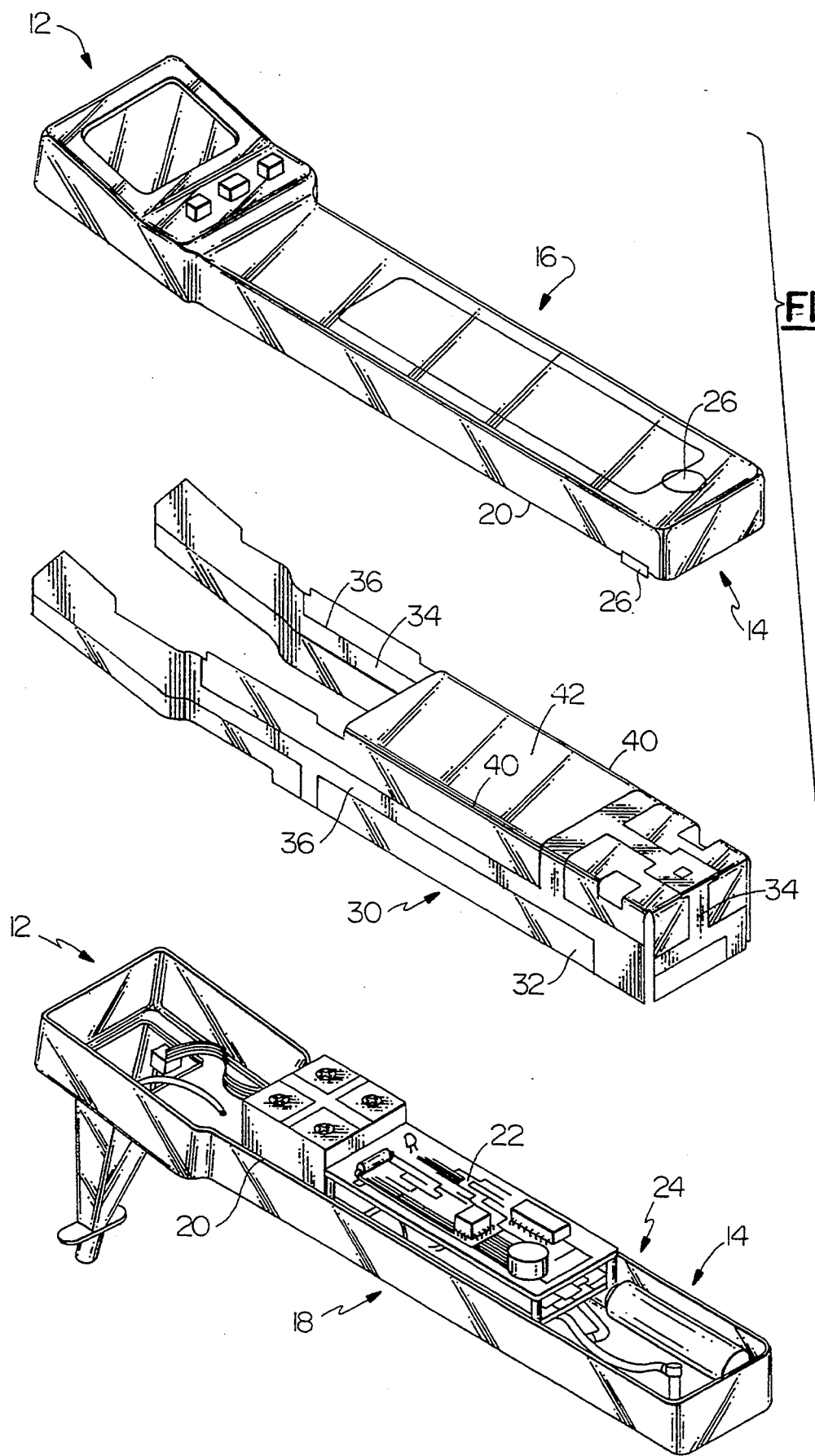
FIG. 3 is an exploded assembly view of the instrument and ESD shield of this embodiment.

With reference to the Drawing and initially FIG. 1, an example of an electronic device is shown as a tympanometric device 10. This device is a sensitive medical diagnostic instrument for conducting tests of a patients ears, in particular for testing their response to sound under positive and negative pressures in the ear canal. An example of a portable, hand held tympanometric device of this type is shown and described in U.S. Pat. No. 4,688,582 granted Aug. 25, 1987. The tympanometric device has a head portion 12 that contains an auricular speculum and a miniature LCD display, and a handle portion 14 that contains a rechargeable power supply and electronic circuitry for automatically controlling a pump and miniature speaker for carrying out a tympanometric examination. The tympanometric device 10 has a two-part housing, composed of a lower portion or base 16 and an upper portion or cover 18, which fit together at a seam or joint 20 that extends longitudinally at each side of the handle portion 14 and head portion 12. The housing is formed of a durable rigid dielectric material, in this case ABS. This material is highly insulative. However, the seam 20 constitutes a leakage path for electrostatic discharge or ESD to enter the inside of the handle portion 14 or the head portion 12.

As shown schematically in FIG. 1, and as also shown in FIG. 3, within the handle portion 14 is contained a circuit board 22 containing CMOS integrated circuit components. These components are highly sensitive to ESD and can be damaged or destroyed if static charge reaches the components.

A battery compartment 24 is situated within the handle portion 14 at a proximal end and contains a set of rechargeable NiCad batteries. Recharging contacts 26 of conductive material on the outer side of the handle portion 14 connect with the rechargeable batteries and permit the unit to be recharged by storing it in a suitable recharging stand.

FIGS. 2 and 3 show an embodiment of an electrostatic discharge (ESD) shield 30. This shield has a substrate 32 in the form of a sheet of insulating material, e.g. Mylar. The substrate 32 is about 0.007 inches thick and is relatively flexible but has an electrical strength on the order of 25 KV. A printed conductive path 34 here is screen printed on the top or outer surface of the substrate 32, employing a screen print nickel ink. Other printing techniques could also be used, such as a transfer print. The conductive path has left and right longitudinal path portions 36 which are at locations that correspond with the seam 20, i.e. a predetermined charge leakage zone, of the casing of the tympanometric device 10.

Contact pads 38 are formed on the conductive path 34 at positions that correspond to the recharging contacts 26. Fold lines 40 or creases permit the shield 30 to be folded to fit inside the tympanometric device casing between the casing and the circuitry 22 to be protected.

An unprinted portion 42 of the substrate 32 is positioned over the sensitive circuitry 22, with the conductive path 34 bypassing this portion.

As shown in FIG. 3, the ESD shield is folded and then installed over the circuit 26 within the housing base 16, and then the cover 18 fits onto the base on top of the shield 30.

The printed conductive path portions 36 absorb any ESD spark that may reach the inside of the handle portion through the seam 20, and guide the spark to a charge sink, e.g. to one of the recharging contacts 26 where the charge can be dissipated harmlessly. Meanwhile, the insulating substrate 32 protects the circuitry 22 from any stray electrostatic discharge.

The path 34 guides the ESD discharge away from the unprinted portion 42, so the risk of harmful discharge into the circuitry is further reduced.

The ESD shield 30 can be installed into equipment as a manufacturing step, or else can be retrofitted into an existing tympanometric device (or other device).

The shield can be used in many other types of devices which need protection from electrostatic discharge, i.e. for all other equipment where sensitive components are housed within a non-conductive casing.

Of course other conductive materials can be employed besides nickel screenprint ink for the conductive path, provided a durable path can be formed at selected regions of the substrate.

While the invention has been shown and described with reference to a preferred embodiment, it should be understood that the invention is not limited to that precise embodiment. Rather many modifications and variations will be apparent to those of skill in the art without departing from the scope and spirit of this invention, as defined in the appended claims.

We claim:

1. In combination, a non-conductive housing and a conductive path ESD shield for protecting components sensitive to high voltage discharge that are located within said housing that has predetermined electrostatic leakage regions, the shield comprising:

a thin sheet of insultative barrier material of high electrical strength and dimensioned to fit within said housing including a first portion disposed in proximity to said components and a second portion extending along said predetermined leakage regions within the housing; and a conductive path formed of a conductive material disposed on an outer side of said sheet of barrier material and located on said second portion of said sheet to extend along said predetermined leakage regions, but with said first portion being of said conductive material so that electrostatic discharge entering said housing passes harmlessly along said conductive path and is kept clear of said first portion and avoids said components.

2. The conductive path ESD shield of claim 1 wherein said thin sheet has a sufficient thickness to provide an electrical strength of at least 1 KV.

3. The conductive path ESD shield of claim 2 wherein said thin sheet has an electrical strength of substantially 25 KV.

4. The conductive path ESD shield of claim 2 wherein said thin sheet has a thickness of 0.010 inches or less.

5. The conductive path ESD shield of claim 2 wherein said shield material is a polyester film.

6. The conductive path ESD shield of claim 1 wherein said conductive path is a conductive ink.

7. The conductive path ESD shield of claim 6 wherein said ink is a nickel ink.

8. The conductive path ESD shield of claim 6 wherein said ink is a graphite ink.

9. The conductive path ESD shield of claim 6 wherein said ink is a silver ink.

10. The conductive path ESD shield of claim 1 wherein at least one contact is mounted on an exterior of said housing with conductors extending through the housing, and said conductive path has a portion in electrical proximity to said at least one contact for returning any electrostatic discharge that has leaked into the housing to the exterior thereof.

11. Conductive path ESD shield for protecting components sensitive to high voltage discharge that are located within a housing that has predetermined electrostatic leakage regions, the shield comprising:

a thin sheet of insulative barrier material of high electrical strength and dimensioned to fit within said housing, including a first portion that corresponds in location to said components and a second portion that corresponds in location to said predetermined leakage regions, but with said first portion being free of said conductive material so that electrostatic discharge entering said housing passes harmlessly along said conductive path and is kept clear of said first portion and avoids said components;

wherein said sheet of barrier material is creased at a predetermined fold line to fit inside said housing, and said conductive path is disposed midway between the fold line and an edge of the sheet to define a zone without said conductive material between said conductive path and said edge.

* * * * *